United States Patent
Cehn

(10) Patent No.: US 6,764,522 B1
(45) Date of Patent: Jul. 20, 2004

(54) PROSTHETIC FOOT

(75) Inventor: Sen-Jung Cehn, Taipei (TW)

(73) Assignee: Teh Lin Prosthetic & Orthopaedic Inc., Taipei (TW)

( * ) Notice: Subject to any disclaimer, the term of this patent is extended or adjusted under 35 U.S.C. 154(b) by 0 days.

(21) Appl. No.: 10/431,852

(22) Filed: May 8, 2003

(51) Int. Cl.⁷ .................................................. A61F 2/66
(52) U.S. Cl. ................................................... 623/55
(58) Field of Search ............................... 623/53–56, 49, 623/52

(56) References Cited

U.S. PATENT DOCUMENTS

| | | | | |
|---|---|---|---|---|
| 592,542 A | * | 10/1897 | Furrer | 623/46 |
| 2,430,584 A | * | 11/1947 | Roche | 623/46 |
| 3,551,914 A | * | 1/1971 | Woodall | 623/53 |
| 5,913,902 A | * | 6/1999 | Geible | 623/55 |
| 6,402,790 B1 | * | 6/2002 | Celebi | 623/38 |

* cited by examiner

*Primary Examiner*—Bruce Snow
(74) *Attorney, Agent, or Firm*—Ladas & Parry

(57) ABSTRACT

A prosthetic foot includes a longitudinal foot body and a biasing unit. The foot body includes front and rear end portions, and a longitudinal cavity between the front and rear end portions and extending inwardly from an upper surface of the foot body. The biasing unit is mounted in the cavity and has first and second ends extending respectively toward the front and rear end portions. The foot body is deflectable to contract the cavity. The biasing unit is subjected to a compression force when the cavity contracts, and restores the foot body to a normal position when the compression force is relieved.

2 Claims, 4 Drawing Sheets

PROSTHETIC FOOT

BACKGROUND OF THE INVENTION

1. Field of the Invention

The invention relates to a prosthetic foot, more particularly to a prosthetic foot which includes a plastic foot body having a cavity that receives a spring and that is contractable upon deflection of the foot body to compress the spring.

2. Description of the Related Art

Referring to FIG. 1, a conventional prosthetic foot 1 is connected to a bottom portion of a limb rod of a prosthetic limb 2. The prosthetic foot 1 is designed to support the weight of the user in such a manner that body balance is maintained when the user is standing on a surface and that the foot 1 can react to the surface in a natural manner with the energy stored during pressing on the surface. However, since this kind of prosthetic foot 1 is made of metal/spring plate, which is highly flexible, the foot 1 cannot provide sufficient rigidity to support the weight of the user.

SUMMARY OF THE INVENTION

Therefore, the object of the present invention is to provide a prosthetic foot that provides good rigidity to resist severe deformation while maintaining sufficient resiliency to permit the prosthetic foot to act like a natural foot.

According to this invention, a prosthetic foot comprises a longitudinal foot body made of a plastic material, and a biasing unit. The foot body includes a front end portion, a rear end portion opposite to the front end portion, an upper surface that extends from the front end portion to the rear end portion, and a longitudinal cavity between the front and rear end portions and extending inwardly from the upper surface. The biasing unit is mounted in the longitudinal cavity, and has a first end extending toward the front end portion, and a second end extending toward the rear end portion. The foot body is deflectable to deform the upper surface and to cause the cavity to contract. The biasing unit is subjected to a compression force when the cavity contracts, and restores the upper surface to a normal position thereof when the compression force is relieved.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
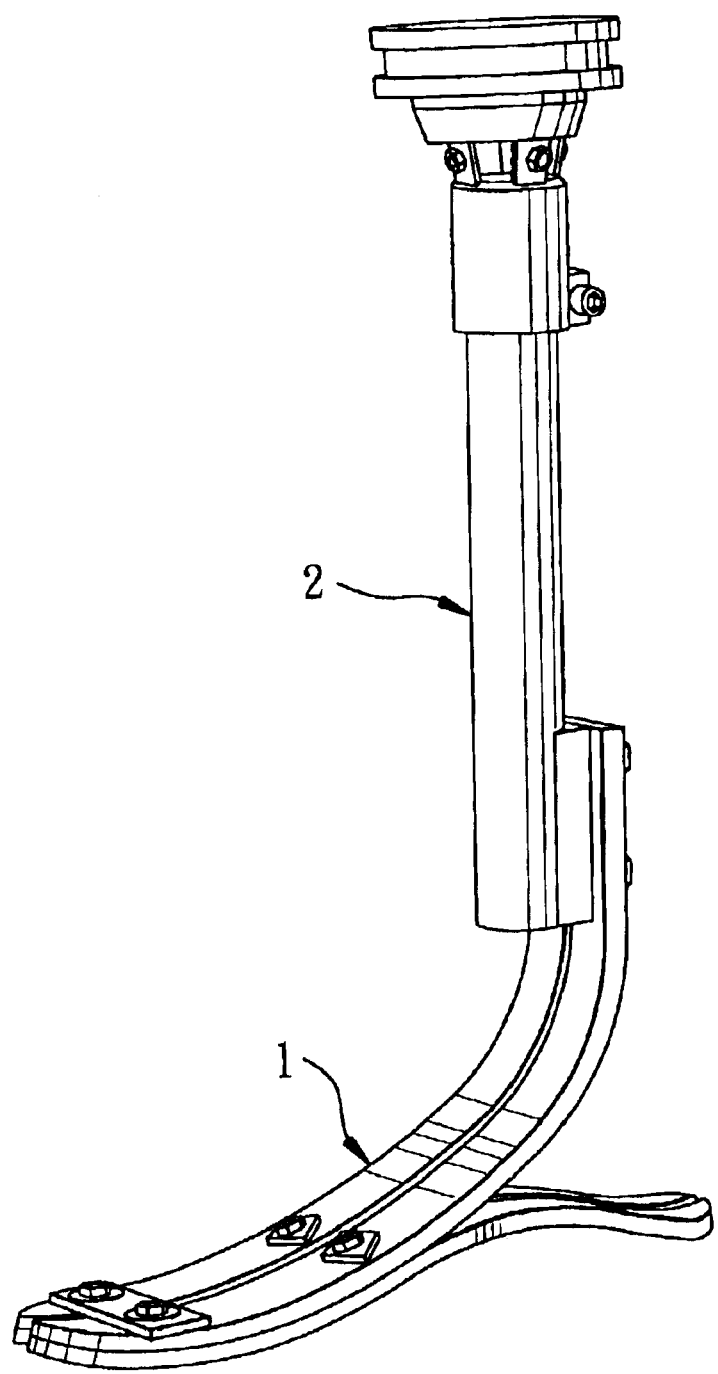
FIG. 1 is a perspective view of a conventional prosthetic foot.
Figure 2:
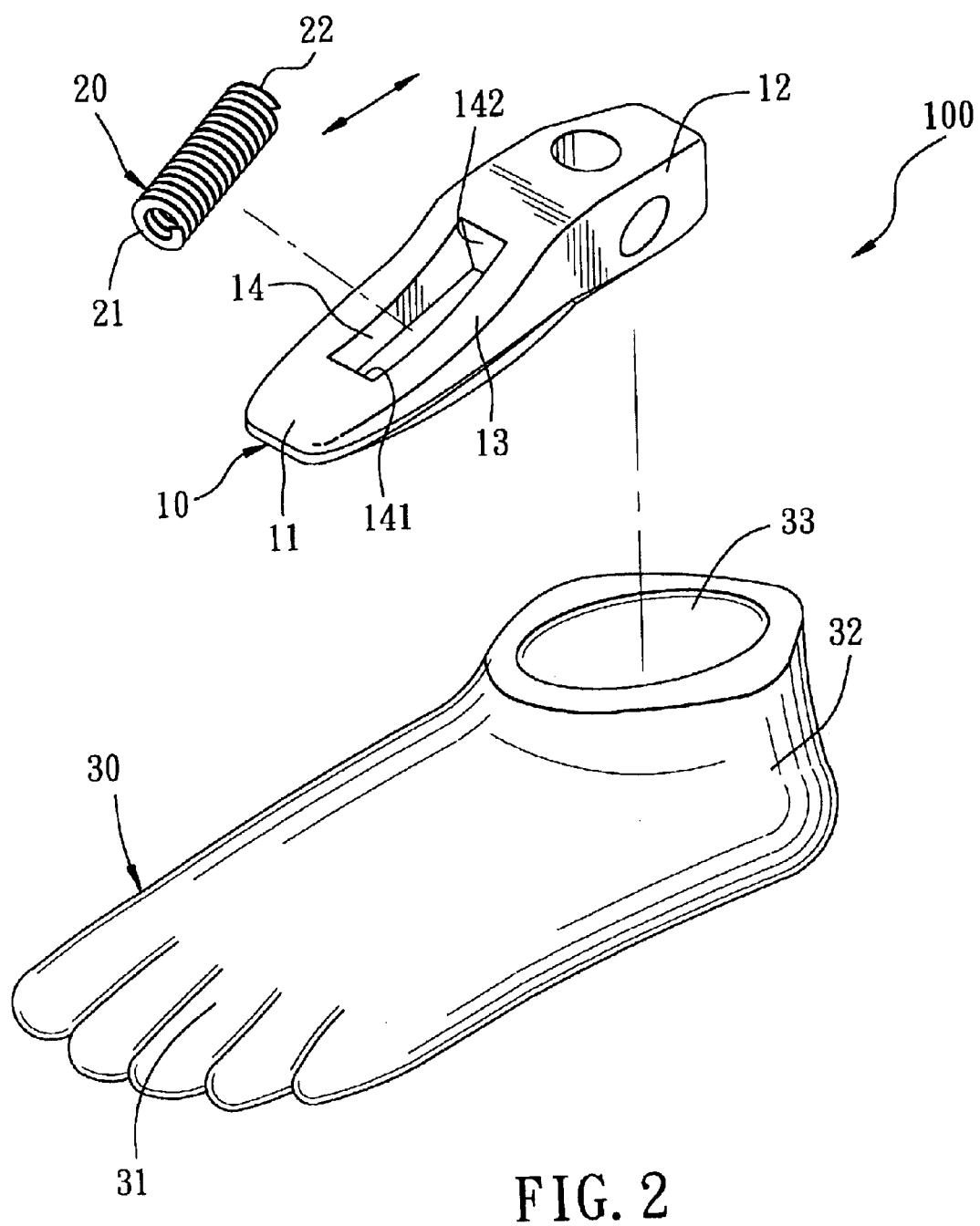
FIG. 2 is an exploded perspective view of the preferred embodiment of a prosthetic foot according to the present invention.
Figure 3:
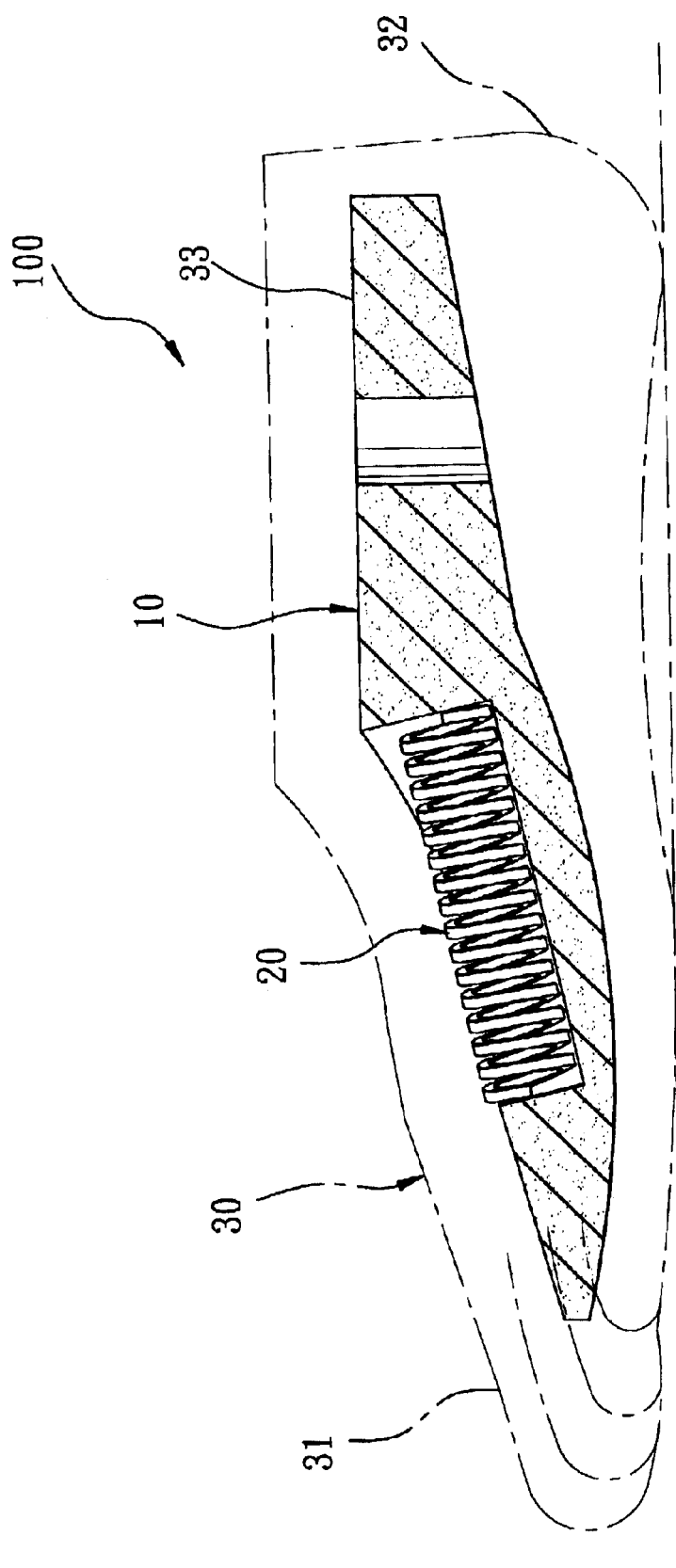
FIG. 3 is a partly sectional view of the preferred embodiment in an assembled state.

Referring to FIGS. 2 and 3, the preferred embodiment of a prosthetic foot 100 according to the present invention is shown to comprise a longitudinal foot body 10 made of a plastic material, a biasing unit, and a shell body 30.

The foot body 10 is made of a plastic material, such as polypropylene, polyethylene, and copolymers thereof, and includes a front end portion 11, a rear end portion 12 opposite to the front end portion 11, an upper surface 13 that extends from the front end portion 11 to the rear end portion 12, and a longitudinal cavity 14 between the front and rear end portions 11, 12 and extending inwardly from the upper surface 13. The cavity 14 has opposite front and rear cavity walls 141, 142.

The biasing unit in this embodiment includes a helical compression spring 20, and is mounted in the longitudinal cavity 14. The spring 20 has a first end 21 extending toward the front end portion 11 of the foot body 10, and a second end 22 extending toward the rear end portion 12 of the foot body 10. The first and second ends 21, 22 abut respectively against the front and rear cavity walls 141, 142 of the longitudinal cavity 14. The shell body 30 is made of a flexible foam material, and includes a toe portion 31, a heel portion 32 opposite to the toe portion 31, and a receiving space 33 extending from a top surface of the heel portion 32 to the toe portion 31. The foot body 10 is inserted into the receiving space 33, and has the front end portion 11 thereof extending toward the toe portion 31.

Figure 4:
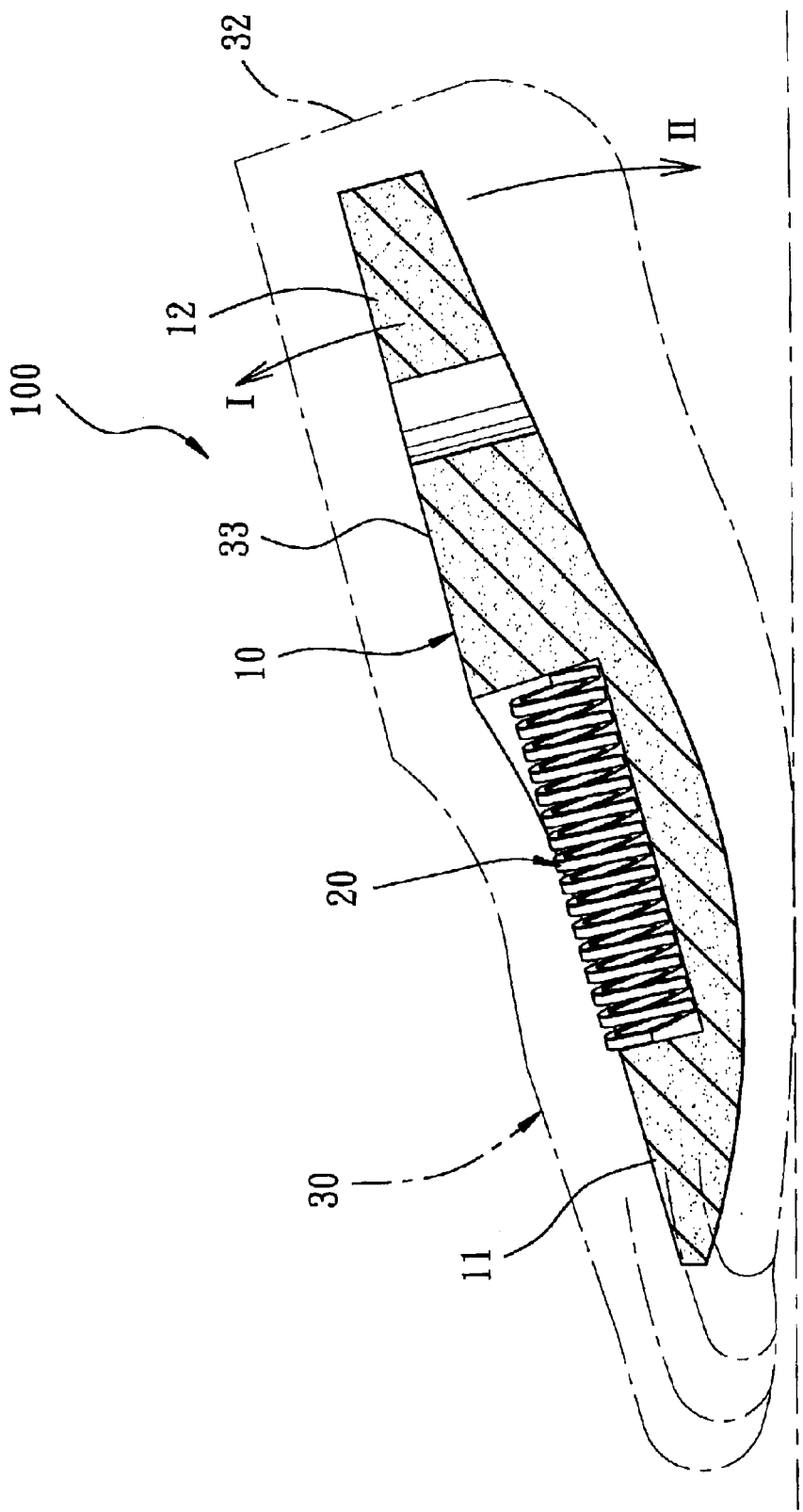
FIG. 4 is the same view as FIG. 3, but illustrating a spring in a compressed state.

Referring to FIG. 4, when the user, after wearing the prosthetic foot 100, strides during walking on the ground surface in a manner in which the toe portion 31 of the shell body 30 presses against the ground surface and the heel portion 32 of the shell body 30 is raised, the rear end portion 12 of the foot body 10 bends upward along a first direction (I) relative to the front end portion 11, thus causing the upper surface 13 to deflect upward and contract the cavity 14. The spring unit 20, at this time, is subjected to a compression force to store energy. Upon continued walking, the foot 100 is lifted, and the ground-pressing force is relieved. In this situation, the spring 20 biases the foot body 10 to move to a second direction (II) to restore the upper surface 13 from a deflected state to a normal state shown in FIG. 3.

As mentioned above, with the spring 20 provided in the cavity 14, the prosthetic foot 100 of the present invention has sufficient resiliency to permit the prosthetic foot 100 to act like a natural foot. Furthermore, since the prosthetic foot 100 does not use the flexible spring plate of the conventional prosthetic foot, the rigidity thereof is improved.

It should be noted that the resiliency of the foot body 10 can be adjusted by selecting a spring 20 with a suitable number of turns. The number of turns of the helical spring 20 determines the resiliency of the foot body 10 to match the weight of the wearer.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. A prosthetic foot comprising:

a longitudinal foot body made of a plastic material, said foot body including a front end portion, a rear end portion opposite to said front end portion, an upper surface that extends from said front end portion to said rear end portion, and a longitudinal cavity between said front and rear end portions and extending inwardly from said upper surface; and a biasing unit mounted in said longitudinal cavity and having a first end extending toward said front end portion and a second end extending toward said rear end portion;

wherein said foot body is deflectable to deform sold upper surface and to contract said cavity, and wherein said biasing unit is subjected to a compression force when said cavity contracts, and restores said upper surface to a normal position thereof when the compression force is relieved;

wherein said cavity has opposite front and rear cavity walls, said first and second ends of said biasing unit abutting respectively against said front and rear cavity walls;

wherein said biasing unit includes a helical compression spring.

2. The prosthetic foot as claimed in claim 1, further comprising a shell body having said foot body mounted therein.

* * * * *